US008293266B2

(12) United States Patent
De Gussem

(10) Patent No.: US 8,293,266 B2
(45) Date of Patent: Oct. 23, 2012

(54) PAROMOMYCIN-SUPPLEMENTED FEED STUFF FOR TURKEY AND USE THEREOF FOR PROPHYLAXIS OF HISTOMONIASIS, REDUCTION OF THE HORIZONTAL SPREADING OF HISTOMONIASIS, AND FOR IMPROVED WEIGHT GAIN AND FEED CONVERSION

(75) Inventor: Koen Luc De Gussem, Aalter (BE)

(73) Assignee: Huvepharma AD, Sofia (BG)

( * ) Notice: Subject to any disclaimer, the term of this patent is extended or adjusted under 35 U.S.C. 154(b) by 161 days.

(21) Appl. No.: 12/524,743

(22) PCT Filed: Feb. 22, 2008

(86) PCT No.: PCT/BG2008/000003
§ 371 (c)(1),
(2), (4) Date: Jul. 28, 2009

(87) PCT Pub. No.: WO2008/106751
PCT Pub. Date: Sep. 12, 2008

(65) Prior Publication Data
US 2010/0137242 A1 Jun. 3, 2010

(30) Foreign Application Priority Data

Mar. 5, 2007 (BG) ........................................ 109831

(51) Int. Cl.
*A23K 1/17* (2006.01)
*A61K 31/715* (2006.01)
(52) U.S. Cl. .......................................... 424/442; 514/61
(58) Field of Classification Search .................. 424/442; 514/61
See application file for complete search history.

(56) References Cited

U.S. PATENT DOCUMENTS

| | | | |
|---|---|---|---|
| 4,000,300 | A | 12/1976 | Mitrovic |
| 4,025,638 | A | 5/1977 | Gyurik et al. |
| 4,046,908 | A | 9/1977 | Haugwitz et al. |
| 4,389,398 | A | 6/1983 | Cooper et al. |
| 6,506,402 | B1 * | 1/2003 | Winstrom ....................... 424/442 |
| 6,761,899 | B1 * | 7/2004 | Winstrom et al. ............. 424/442 |

OTHER PUBLICATIONS

Merriam-Webster Dictionary, Application [Downloaded Apr. 23, 2011] [ Retrieved from internet <URL: http://www.merriam-webster.com/dictionary/application >], 3 pages.*
RxMed: Pharmaceutical information—Humatin [Downloaded Apr. 23, 2011] [Retrieved from internet <URL: http://www.rxmed.com/b.main/b2.pharmaceutical/b2.2.monographs/CPS-%20Monographs/CPS-%20(General%20Monographs-%H)/HUMANTIN.html >], 2 pages.*
Merck Veterinary Manual, Table 02: Drugs for Prevention of Coccidiosis in Poultry [Downloaded Sep. 6, 2011] [Retrieved from internet <URL: http://www.merckvetmanual.com/mvm/htm/bc/tou02.htm >], 1 page.*
Larry R. McDougald Control of Blackhead disease (histomoniasis) ([Downloaded Feb. 24, 2012] [Retrieved from internet <URL: http://www.ces.ncsu.edu/depts/poulsci/conference_proceedings/turkey_days/2008/mcdougald_2008.pdf >], 8 pages.*
H. Jeroch et al. "Studies Investigating the Effect of Antibiotic Supplementation on the Feed Fattening of Broilers Under Conditions of Optimum Nutrition,"ARCH, Tierernahrung, vol. 24, No. 4, 1974, pp. 347-354. (English Translation), 16 pages.*
Beyer and Moritz "Preventing Blackhead Disease in Turkeys and Game Birds," Kansas State University Agricultural Experimental Station and Cooperative Extension Service (Mar. 2000), 2 pages.*
The Merck Veterinary Manual, Coccidiosis ([Downloaded Sep. 6, 2011] [Retrieved from internet <URL: http://www.merckvetmanual.com/mvm/htm/bc/200800.htm >]), 7 pages.*
The Merck Veterinary Manual, Histomoniasis ([Downloaded Sep. 6, 2011] [Retrieved from internet <URL: http: http://www.merckvetmanual.com/mvm/htm/bc/203000.htm >]), 2 pages.*
USDA, Blackhead disease (histomoniasis) in poultry: a critical review ([Downloaded Feb. 24, 2012] [Retrieved from internet <URL: http://openagricola.nal.usda.gov/Record/IND43773732 >]), 1 page.*
International Preliminary Report on Patentability published Sep. 8, 2009 for PCT/BG2008/000003, filed Feb. 22, 2008.
Written Opinion published Sep. 5, 2009 for PCT/BG2008/000003, filed Feb. 22, 2008.
XP002483749, Jinghui Hu et al, "The efficacy of some drugs with known antiprotozoal activity against histomonas meleagridis in chickens", Veterinary Parasitology vol. 121 (2004) pp. 233-238.
XP009101285, William D. Lindquist, "Some Effects of Paromomycin Sulfate on Blackhead in Turkeys", American Journal of Veterinary Research, vol. 32, 1962, pp. 1053-1056.
XP009101284, H. Jeroch et al, "Untersuchungen uber den Einfluss von Antibiotikazusatzen auf die Mastleistung der Broiler bei optimaler Ernahrung", ARCH, Tierernahrung, vol. 24, No. 4, 1974, pp. 347-354.
XP009069336, L.R. McDougald, "Blackhead Disease (histomoniasis) in Poultry: A Critical Review", Avian Diseases, vol. 49, 2005, pp. 462-476.
XP009101378, T. Sreter et al, "Anticryptosporidial Prophylactic Efficacy of Enrofloxacin and Paromomycin in Chickens", The Journal of Parasitology, vol. 88, No. 1, Feb. 2002, pp. 209-210.
XP009101355, Paolo Pastore et al, "Description and validation of an analytical method for the determination of paromomycin sulfate in medicated animal feeds" Analyst, vol. 125, 2000, pp. 1955-1958.
XP002461344, J. Hu et al, "Effect of Anticoccidials and Antibiotics on the Control of Blackhead Disease in Broiler Breeder Pullets" The Journal of Applied Poultry Research, vol. 11, 2002, pp. 351-357.
International Search Report published Sep. 12, 2008 for PCT/BG2008/000003, filed Feb. 22, 2008.
Written Opinion for PCT/BG2008/000003, filed Feb. 22, 2008.

\* cited by examiner

*Primary Examiner* — Scott Long
*Assistant Examiner* — Miriam A Levin
(74) *Attorney, Agent, or Firm* — Martin Felit; Paul D. Bianco; Fleit Gibbons Gutman Bongini & Bianco PL.

(57) ABSTRACT

Disclosed is the continuous supplementation of poultry feeding stuffs with paromomycin and the resulting effects of prophylaxis against histomoniasis, ensuing decrease of mortality and the reduction of horizontal spreading of the disease. Also observed are improved zoo-technical performances, increase in weight gain and feed efficiency, both in healthy as well as diseased birds.

14 Claims, 1 Drawing Sheet

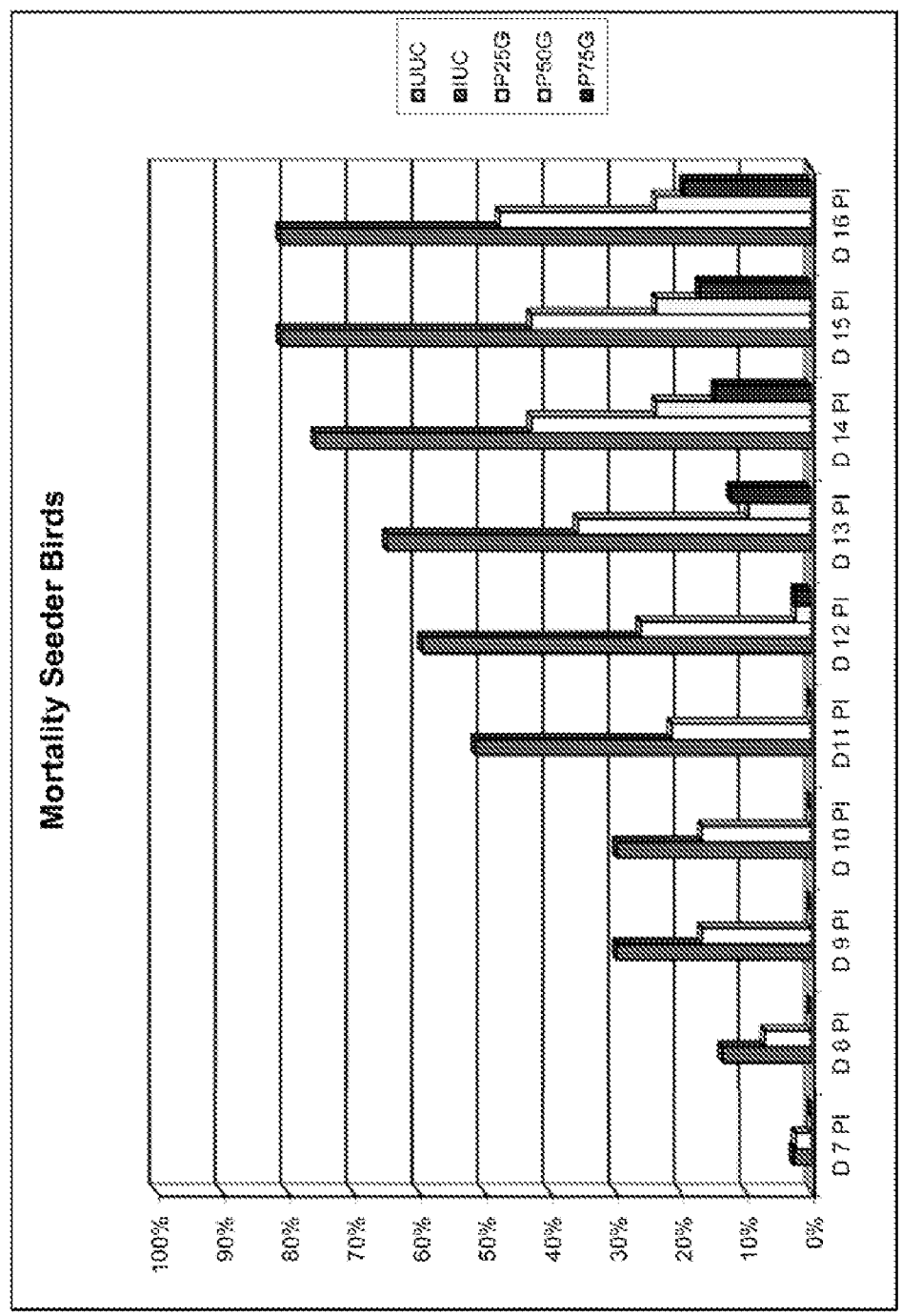

PAROMOMYCIN-SUPPLEMENTED FEED STUFF FOR TURKEY AND USE THEREOF FOR PROPHYLAXIS OF HISTOMONIASIS, REDUCTION OF THE HORIZONTAL SPREADING OF HISTOMONIASIS, AND FOR IMPROVED WEIGHT GAIN AND FEED CONVERSION

CROSS-REFERENCE TO RELATED APPLICATIONS

This application is a U.S. national stage application of International Application No. PCT/BG2008/000003, filed Feb. 22, 2008, which desigfrated designates the United States and which claims priority to Bulgaria Patent application Application No. 109831, filed Mar. 5, 2007, the entire disclosures of which are incorporated herein by reference.

TECHNICAL FIELD

The invention is applied in the veterinary medicine and concerns feeding stuffs for farm and other birds supplemented with paromomycin and their application for prophylaxis against the histomoniasis infection caused by the protozoa *Histomonas* sp., reduction of the horizontal spreading of the disease, as well as for improved weight gain and feed conversion.

BACKGROUND ART

Histomoniasis, also know as blackhead disease, is a protozoan disease affecting farm and other poultry species. The disease causes highest mortality in turkeys affecting frequently the whole flock. In broiler chickens also significant mortality could be observed and be accompanied by high morbidity and decreased zoo-technical performance parameters. Other important poultry species, notably quail, pheasants, guinea fowls are also susceptible to the disease.

Treatment of the Histomoniasis disease through use of chemotherapeutics, most notably nitroheterocyclic compounds, was used in the past, including entheptin, nithiazine, and nitroimidazoles. U.S. Pat. No. 4,000,300 describes the application of aminobenzimidazole derivatives for treatment of histomoniasis; U.S. Pat. No. 4,046,908 describes the use of benzimidasole derivatives; and U.S. Pat. No. 4,025,638 describes use carboalcoxyaminobezimidazole. Also know is the use of arsenic derivatives, like Histostat®, or more specifically nitarzon or 4-nitrophenyl arsenic acid. However, on the ground that these compounds are suspected carcinogens, and their use leads to the accumulation of carcinogenic products in the treated animals, their use was prohibited or limited to a large extend in the USA, Europe, and other important turkey growing regions. Currently, no preventive histomonostat as feed additive or any therapeutic drugs are authorized in the EU to either prevent or to treat histomoniasis in affected flocks. As a result we see a number of reports for new appearances of histomoniasis in turkey and other flocks.

Also known is the use of coccidiostats (for example monensin, salinomycin, diclasuril and etc.) through the whole growth cycle of farm birds species in order to protect from coccidiosis or histomoniasis, but it has been shown that their use has no effect with respect to histomoniasis (6).

Also known are attempts to use of paromomycin as a chemotherapeutic agent for treatment of histomoniasis (3). The disadvantage is the estimated high dose and long treatment needed to achieve limited results. It was demonstrated that when fed continuously at 1000-2000 ppm in feed it reduced the mortality of infected birds, but at these doses side effects due to the use of paromomycin were observed—notably lesions and hypertrophy of the liver. In these trials the infection was achieved by direct oral inoculation of the birds with infected embryonated *Heterakis gallinarum* eggs and the effect of applying paromomycin on the horizontal spreading of the disease from infected to healthy birds was not evaluated. It has also been attempted to use paromomycin as a chemotherapeutic agent in broiler chickens. Its use in-vivo was rendered ineffective when applied at 200 and 400 ppm in broilers (4).

DISCLOSURE OF INVENTION

The purpose of the present invention is through supplementing feeding stuffs for farm and other poultry species with paromomycin to achieve prophylaxis of the histomoniasis, reduction of the horizontal spreading of the disease, as well as for improved weight gain and feed conversion.

Histomoniasis, also know as blackhead disease, is a protozoan disease affecting poultry species. The disease causes high mortality in turkeys affecting frequently the whole flock. Under farming conditions there are reports for severe outbreaks in both turkeys reared for growth and for reproduction. The disease could spread quickly and mortality of close to 100% could be reached in weeks time. In chickens, outbreaks in broiler breeder pullets and in layer pullets are common and mortality could reach 10-20%. As with other protozoan infections, there is a notable decrease in zootechnical performance parameter. Overall in chickens blackhead is as severe as coccidiosis, which is already considered the condition with greatest impact on economic performance.

Histomoniasis is caused by the protozoan microorganism *Histomonas meleagridis*. Is life cycle is complex and could involve an intermediate host. Two factors related to the epidemiology of blackhead disease must be considered in the explanation of its spreading in poultry species:

1) the transfer of histomoniasis from flock to flock or between animals by an intermediate host vector—the worm *Heterakis gallinarum*, and
2) the horizontal or lateral transmission of Histomoniasis from bird to bird, enabling the rapid spread of the disease through the flock in the turkey or other bird-growing facility even without the presence of an intermediate host. (1).

Until recently it was considered that the transfer of the disease by the intermediate host, the worm *Heterakis gallinarum*, was the dominating and most economically important route for spreading of the disease in poultry species. However, the explosive epidemic spread of the disease, especially in turkeys, cannot be explained only by this mechanism. Furthermore, horizontal spreading of histomoniasis in these species could be observed in a worm free environment. Most recently (2) it was shown that within the flock of turkeys the disease can be spread by the phenomenon "cloacal drinking." This is the transfer of liquid or suspended materials placed on the vent lips into the bursa and the ceca. The transfer is facilitated by retrograde movement of urine from the cloaca caused by reverse peristalsis. It has been demonstrated in controlled trials that through this mechanism (i) turkey birds can be infected by a live culture and (ii) the disease can be efficiently transferred horizontally from the feces of infected birds to healthy birds.

This combination of infection ways makes it de facto impossible to predict, let alone to control, the kinetics of this disease in a population. This is reflected by the occurrence of different clinical pictures of the disease: varying from very mild, slowly passing through a flock, over very acute and severe outbreaks, to outbreaks in which only a part of the house is affected while another part which is very rudimentary separated from the affected part might not get the disease.

The cloacal drinking phenomenon is determined by the physiology of avian species and is observed not only in turkeys, but also in chickens and other poultry species. While at this moment the lateral spreading of Histomoniasis through the cloacal drinking has been demonstrated in turkey only, all prerequisites for realization of this mechanism are available to the other poultry species. Poultry species also susceptible to the disease are quail, pheasants, guinea fowls and others.

There are three possibilities to control a disease: vaccination, treatment of diseased animals with chemotherapeutics, and prophylaxis and metaphylaxis Use of vaccines is based on inducing an immune response in the treated birds against the causative agent of the disease. There have not been discovered and developed vaccines against *Histomonas meleagridis*. There are vaccines developed for somewhat similar diseases, for example against coccidiosis caused by *Eimeria* sp. However, considering the very high susceptibility of some poultry species, most notably the turkey species, to infection by *Histomonas meleagridis* it remains doubtful if vaccination could be a successful approach.

Treatment of the disease through use of chemotherapeutics involves application of a chemotherapeutic agent to the diseased/infected animals. As in the case of poultry species in farm conditions it is difficult and impractical and even impossible to separate diseased animals from healthy animals, the chemotherapeutic agent could be applied to the whole flock. A successful chemotherapeutic should effectively kill or stop the development of the causative microorganism or parasite. Chemotherapeutic agents are applied at a predetermined dose for a short period of time sufficient to kill the causative microorganism or parasite.

Prophylaxis is defined as the application of a prophylactic agent to a healthy animal or a whole flock of healthy species before the onset of an infection with the aim of preventing the introduction of an infection or spread of the disease. In the case when the prophylactic treatment is applied only through a period when the population is most susceptible or most likely to develop a disease, it is called metaphylaxis. The application of the prophylactic agent usually starts as soon as possible, frequently in the very beginning of the life cycle of the animals, in order to prevent the introduction of the infection.

Paromomycin is an amino-glycoside antibiotic produced by microorganisms of the *Streptomyces* sp. genus. It is structurally related to neomycin, streptomycin and kanamycin and has a broad spectrum of activity, including activity against protozoa, bacteria, and cestodes.

Surprisingly, in a series of experiments for evaluation of compounds as prophylactic agents for prevention of Histomoniasis in turkey it was discovered that the continuous application of paromomycin in feed in dosages below 1000 ppm, in the range 10-750 ppm, had a significant effect in (i) reducing the mortality of infected birds; (ii) significant reduction in the horizontal spread of the disease from infected to healthy birds and (iii) improving the growth performance of the infected and non-infected animals. The antibiotic was applied continuously in the feed from day 0 for several weeks during the sensitive period.

There are two main parameters which are followed to evaluate the effect of different treatments of Histomoniasis—mortality rate and lesions scoring. Mortality has to be associated with the disease and not caused by another factor. This is proven by necropsy and observation of the clinical signs associated with the disease. Lesions on the liver and ceca are typical signs of the Histomoniasis infection. The quantitative evaluation of these lesions is termed scoring and is useful in the evaluation of the degree of the disease/infection.

As explained above, the reduction of mortality of infected birds as a result of application of paromomycin has been previously observed. However, the dosage tested exceeded 1000 ppm which is economically impractical and the use of paromomycin in this high concentration lead to certain toxicity effects, which are typically observed when applying amino-glycosides at high dose. Tests at 200 and 400 ppm in broilers have shown that paromomycin had no effect on both mortality and lesion scoring.

Thus it was surprising to discover that in practice a significant effect in reducing the mortality of infected birds could be achieved when paromomycin was applied continuously in the feed at dosages less than 1000 ppm. This discovery can be attributed to, most importantly, the employment of inoculation method which more correctly represents the field conditions, as well as to the more extensive study protocol used—the test of wider range of dosages and the greater number of experimental units employed.

The second effect of the current application is the reduction of the spread of the disease from infected to healthy birds. Previous research has focused on disease models using *Heterakis gallinarum* as an intermediate vector, as this was thought to be the dominating mechanism for spreading of the disease. However, it has been demonstrated that disease transfer without intermediate host is possible and for the turkey-growing facilities the horizontal transfer of histomoniasis between infected and healthy animals is important for limiting the spread of the disease. It is previously demonstrated that there could be no significant relationship between the number of already infected animals and the number of newly infected animals (5). This phenomenon is in conformance with the "cloacal drinking" as a mechanism for disease transfer—the infected feaces of one animal can "inoculate" with *histomonas* a great number of birds from the same flock.

We discovered that the continuous application of paromomycin in the turkey feed in dosages below 1000 ppm leads to significant reduction in, and even could eliminate, the horizontal spread of the disease from infected to healthy birds. The observed dosage-related effect, while not scientifically explained yet, suggests the presence of an action mechanism exerted by the antibiotic on the mode of transfer of histomoniasis by the important step in the field mechanism.

It is further an object of this invention the observed improvement of zoo-technical performance when paromomycin is continuously applied in the feed. Zoo-technical performance is measured by two main parameters: weight gain and feed conversion. Weight gain represents the increase in weight of the reared animals. It can be improved if animals reach faster certain pre-specified weight, or if at the end of a pre-specified period the animals reach greater weight. The feed conversion efficiency is the ratio of the used feed and the achieved weight. The higher feed conversion ratio is, the less effective is the performance of the farm, as it takes more feed to achieve the same weight of product. While the growth promoting effect of antibiotics in animal production is known, the use of amino-glycosides is typical as therapeutic agents and for a short period. Their long-term application is not desired due to toxicity side effects, in particular liver toxicity.

However, it was discovered that the continuous application of paromomycin in the turkey feed in dosages below 1000 ppm leads to improving the growth performance and feed efficiency of the infected and non-infected animals. The observed effect is dosage related when paromomycin is applied continuously in the feed at concentrations below 1000 ppm.

While the most convenient way of application of a treatment agent is by mixing it with the feed, it shall be clear for the skilled in the art, that the effect of an orally administered agent is comparable when it is applied in the feed or in the water or as an independent oral dosage form, as long as the same intake is provided and achieved. Accordingly, in the context of the present invention, supplementation of paromomycin in feeding-stuffs includes supplementation of the feed, the water, or the oral administration of a paromomycin containing form providing the required amount of intake per body weight per day. In such a way, one can estimate that an application of paromomycin in the range of 10 to 750 ppm in feed corresponds approximately to a dosage of 5 to 100 mg of paromomycin per kg body weight per day, and this dosage can be achieved by inclusion of the appropriate amount of paromomycin in the drinking water or in liquid feed.

It shall also be noted that in different conditions different dosages could be optimal. It has been demonstrated that significant effect on mortality, reduction of horizontal spreading of the disease and weight gain are achieved with inclusion rates of 750 ppm and as low as 250 ppm. However these results were achieved under conditions of heavy challenge by a highly pathogenic strain of *Histomonas meligridis*. It can easily be concluded that in conditions of no danger of disease outbreak or when less pathogenic strains of *Histomonas* are ambiently present, the dosage for providing defense against spread of the disease could be lowered significantly. However, too low inclusion rate of an antibiotic can prompt the development of resistance and cause reduction of efficacy. Accordingly, the preferred dose under the current invention is below 1000 ppm, in the range 10-750ppm.

The application regimen would require constant pressure of the agent applied for prophylaxis or metaphylaxis. Survey on the outbreak of Histomoniasis show that a very high number of cases were found among birds from 4 to 8 weeks of age, but surprisingly some of them arose in younger (3 weeks) and much older birds (up to 17 weeks). The mortality rate was mostly below 10% but is above 30% in nearly 20% of cases (7). Accordingly, if paromomycin is applied as a metaphylactic agent, it shall be applied for at least one week during the sensitive period, more preferably it shall be applied starting not later than the third ($3^{rd}$) week and continue to at least 8 weeks of age, even more preferably in order to avoid mortality incidents and reduce the number of infected animals in the flock its use shall start from day 0 and continue to the end of growth period.

Paromomycin, similarly to other amino-glycosides, is most often available as a sulphate salt. However, other pharmaceutical forms are also available or could be achieved. Accordingly, for convenience and clarity application rates and dosages are expressed as the amount of paromomycin applied as a base. This way all dosages are independent of the form in which the active compound paromomycin was supplied. The object of this invention is by no means limited to application of paromomycin in any particular form, but rather includes all pharmaceutically feasible salts and other derivatives, including not purified and technical grade intermediates containing paromomycin.

The following examples illustrate the use of the invention, without restricting it in any way.

EXAMPLE 1

The objective of the study was to investigate the susceptibility of a European *Histomonas meleagridis* strain to paromomycin supplemented through the feed at different doses in turkeys. Inclusion levels were 500 ppm and 1000 ppm of paromomycin (as base) in the feed. One hundred sixty (160) one day old turkey poults were enrolled in the study and randomly allocated to 4 groups of 40 animals in one house. During the whole study (day 1 to day 55), Group 1 received standard turkey feed without supplementation (negative control), whereas Group 2 received feed supplemented with Histostat® at a concentration of 187.5 ppm nitarsone as a positive control. Test groups Group 3 and Group 4 received feed supplemented with PAROMOMYCIN at 500 g/MT and 1000 g/MT respectively. On day 40, Groups 1, 2, 3, and 4 were inoculated intracloacally with strain, HNA.CO.A.L1 isolated from an outbreak of histomoniasis in turkey breeders in France in July 2006. From that day on, the birds were clinically observed on a daily base. On day 55, all remaining birds were euthanized, and cecum and liver lesions observed.

Table I gives the development of mortality due to the histomoniasis infection. It is clearly seen that even the low dose of paromomycin provides significant protection compared to the infected untreated group. The same conclusion is drawn from the lesion scoring results provided in Table II. The results of this trial demonstrate that paromomycin could provide histomoniasis prevention effect when included in the feed at doses below 1000 ppm. The zoo-technical parameters are listed in Table III. More details on the effect of its inclusion in the feed are provided in Example 2.

EXAMPLE 2

The objective of the study was to investigate the susceptibility of an European *Histomonas meleagridis* strain to different doses of paromomycin in turkeys, its application as a prophylaxis agent and the effect on the horizontal spread of histomoniasis between infected (seeder) birds and non-infected (contact) birds. Further, the effect of paromomycin on weight gain in all groups was investigated.

At arrival, the 750 one-day old turkeys were randomly allocated to one of the five treatment groups (i.e. 25 animals per pen), half of pens were filled with males, the other half with females:

Treatment 1=Uninfected unmedicated group (UUC)
Treatment 2=Infected Untreated Control group (IUC)
Treatment 3=Infected, 250 ppm paromomycin sulphate in feed (P25G);
Treatment 4=Infected, 500 ppm paromomycin sulphate in feed (P50G);
Treatment 5=Infected, 750 ppm paromomycin sulphate in feed (P75G);

Note: the dosage of paromomycin is given as paromomycin sulphate. These quantities expressed as a base correspond respectively to 187, 375 and 562 ppm.

In-feed medication in Treatment 3, 4 and 5 started on study day 1 and lasted until study day 45 (end of study). Animals in all Groups 2, 3, 4 and 5 were challenged with *Histomonas meleagridis* on study day 29. Animals from all groups were clinically examined daily from the day of challenge (day 29) until the end of the study (day 45). On day 29, Treatments 2, 3, 4 and 5 were inoculated intracloacally with *Histomonas meleagridis* strain HNA.CO. A.L1. This strain had been isolated from a severe outbreak of histomoniasis in turkey breeders in France in the summer of 2006. In order to mimic the field situation and to study the effect of paromomycin on the horizontal spread of the disease, 7 turkeys per pen were inoculated. Previous research (McDougald, 2005) has shown that the disease afterwards spreads through the pen. Inoculation was done with a syringe with plastic tube which was inserted in the cloaca. Single Inoculation Dose was 400.000 histomonads. This procedure was repeated after a 15 minutes interval, in order to minimize the risk for unsuccessful challenge by early defecation. In total the Seeder birds received 800.000 histomonads.

Table IV gives the mortality data in this experiment. The seeder birds mortality data is better represented on Figure I. It is evident that even the lowest dose of paromomycin provides significant protection to infection. There is a clear dosage dependent relationship between the disease effect on the animals and the inclusion rate of paromomycin. This trend is confirmed by the lesion scores of the seeder birds given in Table V. The lower lesion scores prove the reduction of damages to the gastro-intestinal tract in the presence of an infection.

It is important to consider the mortality of the contact birds due to histomoniasis. The total mortality data is given on Table IV. In the infected untreated group (IUC) there is 30% mortality as a result of horizontal spreading of the disease from the seeder to the contact birds.

In all treated groups, there was no mortality in the contact birds due to histomoniasis, which was established through the lack of the typical lesions during necropsy. This clearly indicates the elimination of the horizontal transfer of the disease from seeder to healthy animals, which could be considered as the prevailing mechanism for disease outbreaks in farming conditions.

Finally, Table VI provides the overall zoo-technical performance data for the groups in the Experiment. The improvement of body weight at the end of the experimental period is significant for all paromomycin treated groups when compared to the untreated and uninfected control (UUC). This improvement measures between 15.3% for group P25G to 31.2% for the P75G group. At the same time the feed conversion ratio, which is the ratio between utilized feed per unit weight gain, is significantly decreased in the paromomycin treated groups. This decrease measures between 7.2% for group P25G to 10.4% for the P75G group.

The achieved increase in zoo-technical performance is statistically significant and surprisingly high, considering that the typical use of antibiotics as growth promoters achieves ~5% increase in weight gain and 5% decrease in feed conversion.

Literature:
(1) McDougald, L. R. 2005, Blackhead Disease (Histomoniasis) in Poultry: A Critical Review, Avian Diseases, 49:462-476;
(2) Hu, J., L. Fuller, L. R. McDougald, 2004, Infection of turkeys with *Histomonas meleagridis* by the cloacal drop method, Avian Dieseases, 48:746-750
(3) Lindquist, W. D., 1962; Some Effects of Paromomycin Sulfate on Blackhead in Turkeys, Am. J. Vet. Res., vol. 23
(4) Jinghui, H., 2002;
(5) Hu, J., L. Fuller, L. R. McDougald, 2005, Blackhead disease in turkeys: Direct transmission of *Histomonas meleagridis* from bird to bird in a laboratory model. Avian Diseases, 49:328-331;
(6) Hu, J. and L. R. McDougald, 2002, Effect of anticoccidials and antibiotics on the control of blackhead disease in broiler breeder pullets, J. Appl. Poult. Res., 11:351-357.
(7) Callait-Cardinal M. P., Leroux S., Chauve C. M., Le Pottier G. & Zenner L. 2003, Incidence of histomoniasis in turkeys in France since 2003: measures of disease frequency and first approach to analyzing survival data.
(8) U.S. Pat. No. 4,000,300
(9) U.S. Pat. No. 4,046,908
(10) U.S. Pat. No. 4,025,638

Tables:

TABLE I

Example 1: Mortality due to Histomoniasis

| Days post challenge | Infected Unmedicated Group 1 (n = 28) | Infected Histostat ® Group 2 (n = 38) | Infected P50G Group 3 (n = 35) | Infected P100G Group 4 (n = 35) |
|---|---|---|---|---|
| 1 | 0 | 0 | 0 | 0 |
| 2 | 0 | 0 | 0 | 0 |
| 3 | 0 | 0 | 0 | 0 |
| 4 | 0 | 0 | 0 | 0 |
| 5 | 0 | 0 | 0 | 0 |
| 6 | 0 | 0 | 0 | 0 |
| 7 | 7 | 0 | 0 | 0 |
| 8 | 9 | 0 | 0 | 0 |
| 9 | 3 | 0 | 0 | 0 |
| 10 | 3 | 0 | 0 | 0 |
| 11 | 2 | 0 | 1 | 0 |
| 12 | 1 | 1 | 2 | 0 |
| 13 | — | 0 | 0 | 0 |
| 14 | — | 0 | 4 | 2 |
| 15 | — | 1 | 1 | 0 |
| Total | 25 | 2 | 8 | 2 |
| Rate (%) | 96.15% | 5.26% | 22.86% | 5.71% |

TABLE II

Example 1: Lesions at Necropsy

| Group | Mean lesion score | |
|---|---|---|
| | Caeca | Liver |
| Infected Unmedicated Group 1 | 3.89 | 3.86 |
| Infected Histostat ® Group 2 | 1.26 | 1.13 |
| Infected P75G Group 3 | 2.11 | 1.77 |
| Infected P150G Group 4 | 1.51 | 1.43 |

TABLE III

Example 1: Zootechnical Parameters

| | Infected Unmedicated Group 1 | Infected Histostat ® Group 2 | Infected P50G Group 3 | Infected P100G Group 4 |
|---|---|---|---|---|
| Average body weight prior to challenge (kg) (40 days old) | 1.78 | 1.92 | 2.07 | 2.28 |
| Average body weight at necropsy (kg) (days old) | 1.44 | 3.20 | 3.09 | 3.60 |
| Weight gain between days 29 and 43 (%) | −23.09% | 39.98% | 32.96% | 36.74% |

TABLE IV

Example 2: Mortality data

| Days post challenge | UUC Group Seeders | UUC Group Contact birds | IUC Group Seeders | IUC Group Contact Birds | P25G Group Seeders | P25G Group Contact Birds | P50G Group Seeders | P50G Group Contact Birds | P75G Group Seeders | P75G Group Contact Birds |
|---|---|---|---|---|---|---|---|---|---|---|
| 1 | — | 0 | 0 | 0 | 0 | 0 | 0 | 0 | 0 | 0 |
| 2 | — | 0 | 0 | 0 | 0 | 0 | 0 | 0 | 0 | 0 |
| 3 | — | 0 | 0 | 0 | 0 | 0 | 0 | 0 | 0 | 0 |
| 4 | — | 0 | 0 | 0 | 0 | 0 | 0 | 0 | 0 | 0 |
| 5 | — | 0 | 0 | 0 | 0 | 0 | 0 | 0 | 0 | 0 |
| 6 | — | 0 | 0 | 0 | 0 | 1 | 0 | 0 | 0 | 0 |
| 7 | — | 0 | 1 | 0 | 1 | 0 | 0 | 0 | 0 | 0 |
| 8 | — | 0 | 4 | 1 | 2 | 0 | 0 | 0 | 0 | 0 |
| 9 | — | 0 | 6 | 0 | 4 | 0 | 0 | 0 | 0 | 0 |
| 10 | — | — | — | — | — | — | — | — | — | — |
| 11 | — | 1 | 8 | 5 | 2 | 0 | 0 | 0 | 0 | 0 |
| 12 | — | 1 | 3 | 7 | 2 | 1 | 1 | 0 | 1 | 0 |
| 13 | — | 1 | 2 | 7 | 4 | 0 | 3 | 0 | 4 | 0 |
| 14 | — | 2 | 4 | 7 | 3 | 0 | 6 | 2 | 1 | 0 |
| 15 | — | 2 | 2 | 1 | 0 | 0 | 0 | 0 | 1 | 0 |
| 16 | — | 3 | 0 | 6 | 2 | 0 | 0 | 0 | 1 | 0 |
| Total | — | 10 | 30 | 34 | 20 | 2 | 10 | 2 | 8 | 0 |
| Rate (%) | — | 6.99 | 81.08 | 32.69 | 47.62 | 2.15 | 23.81 | 2.00 | 19.51 | 0.00 |

TABLE 5

Example 2: Seeders mean lesion score at necropsy

| Goup | Caeca | Liver |
|---|---|---|
| UUC | | |
| IUC | 3.27 | 3.22 |
| P25G | 2.05 | 2.00 |
| P50G | 0.95 | 0.95 |
| P75G | 0.80 | 0.78 |

TABLE VI

Experiment 2, The zootechnical performance

| | BW-1 d. gram | BW-30 d. gram | daily feed int. 1-30 d. gram | Weight gain. 1-30 d. gram | feed conv. 1-30 d | BW-43 d. gram | daily feed int. 31-43 d. gram | Weight gain. 31-43 d. gram | feed conv. 31-43 d | daily feed int. 1-43 d. gram |
|---|---|---|---|---|---|---|---|---|---|---|
| 1 | | | | | | | | | | |
| Tot. average | 60 | 824 | 37.7 | 25.5 | 1.478 | 1450 | 96.9 | 48.1 | 2.015 | 55.1 |
| Av. males | 60 | 896 | 40.1 | 27.9 | 1.437 | 1553 | 98.5 | 50.5 | 1.950 | 56.9 |
| Av. females | 59 | 753 | 35.2 | 23.1 | 1.524 | 1347 | 95.3 | 45.7 | 2.085 | 53.3 |
| 2 | | | | | | | | | | |
| Tot. average | 59 | 832 | 38.2 | 25.8 | 1.481 | 1273 | 84.3 | 33.9 | 2.487 | 51.4 |
| Av. males | 59 | 886 | 40.1 | 27.6 | 1.453 | 1361 | 88.2 | 36.5 | 2.416 | 54 |
| Av. females | 59 | 778 | 36.4 | 23.9 | 1.523 | 1184 | 80.4 | 31.3 | 2.569 | 48.9 |
| 3 | | | | | | | | | | |
| Tot. average | 59 | 873 | 38.3 | 27.2 | 1.408 | 1672 | 111 | 61.4 | 1.808 | 59.4 |
| Av. males | 60 | 925 | 40.2 | 28.8 | 1.396 | 1789 | 116 | 66.5 | 1.744 | 61.7 |
| Av. females | 58 | 822 | 36.5 | 25.5 | 1.431 | 1555 | 106 | 56.4 | 1.879 | 57 |
| 4 | | | | | | | | | | |
| Tot. average | 59 | 910 | 39.2 | 28.4 | 1.380 | 1815 | 121.4 | 69.6 | 1.744 | 63.8 |
| Av. males | 59 | 961 | 40.4 | 30.1 | 1.342 | 1908 | 124.8 | 72.9 | 1.712 | 65.2 |
| Av. females | 60 | 860 | 38 | 26.7 | 1.423 | 1723 | 118 | 66.4 | 1.777 | 62.5 |

TABLE VI-continued

Experiment 2, The zootechnical performance

| 5 | | | | | | | | | | |
|---|---|---|---|---|---|---|---|---|---|---|
| Tot. average | 59 | 921 | 40.1 | 28.7 | 1.397 | 1902 | 126.6 | 75.5 | 1.677 | 65.6 |
| Av. males | 59 | 962 | 41.3 | 30.1 | 1.372 | 1984 | 130.3 | 78.7 | 1.656 | 67.5 |
| Av. females | 58.5 | 880 | 38.9 | 27.4 | 1.420 | 1820 | 123 | 72.3 | 1.701 | 63.7 |

| | Weight gain. 1-43 d. gram | feed conv. 1-43 d | Total mortality. % | Production value | caecum lesie | liver lesie | Mortality 1-31 d. % | Mortality 31-43 d. % |
|---|---|---|---|---|---|---|---|---|
| 1 | | | | | | | | |
| Tot. average | 32.3 | 1.706 | 10 | 170 | 0 | 0.01 | 4.7 | 5.6 |
| Av. males | 34.7 | 1.640 | 16 | 179 | 0 | 0 | 6.7 | 9.8 |
| Av. females | 29.9 | 1.783 | 4 | 161 | 0 | 0.01 | 2.7 | 1.3 |
| 2 | | | | | | | | |
| Tot. average | 28.2 | 1.823 | 41.6 | 90 | 1.05 | 0.85 | 3.3 | 39.4 |
| Av. males | 30.3 | 1.782 | 45.9 | 91 | 0.96 | 0.79 | 2.7 | 44.2 |
| Av. females | 26.2 | 1.866 | 37.3 | 88 | 1.13 | 0.91 | 4 | 34.6 |
| 3 | | | | | | | | |
| Tot. average | 37.5 | 1.584 | 23.9 | 180 | 0.7 | 0.63 | 8.7 | 16.7 |
| Av. males | 40.2 | 1.535 | 32 | 180 | 0.94 | 0.83 | 12 | 22.3 |
| Av. females | 34.8 | 1.638 | 15.7 | 180 | 0.45 | 0.44 | 5.3 | 11.1 |
| 4 | | | | | | | | |
| Tot. average | 40.8 | 1.564 | 13.3 | 226 | 0.28 | 0.29 | 5.3 | 8.3 |
| Av. males | 43 | 1.516 | 12 | 247 | 0.22 | 0.24 | 4 | 8 |
| Av. females | 38.7 | 1.615 | 14.7 | 206 | 0.34 | 0.34 | 6.7 | 8.6 |
| 5 | | | | | | | | |
| Tot. average | 42.9 | 1.529 | 10.7 | 251 | 0.24 | 0.24 | 5.3 | 5.7 |
| Av. males | 44.8 | 1.507 | 9.3 | 269 | 0.25 | 0.25 | 4 | 5.6 |
| Av. females | 41 | 1.554 | 12 | 232 | 0.24 | 0.24 | 6.7 | 5.9 |

The invention claimed is:

1. A method for preventing infection with or spread of histomoniasis in healthy turkey or in a flock of healthy turkey, the method comprising:
    formulating a feed stuff for turkey comprising feed supplemented with paromomycin in an amount sufficient to provide prophylaxis of histomoniasis; and
    feeding the feed stuff to the healthy turkey or flock of healthy turkey continuously from day 0 until slaughter or at least for more than one week; whereby infection or spread of histomoniasis in the healthy turkey or in the flock of healthy turkey is prevented.

2. The method according to claim 1, wherein the feeding is applied during a time period when the healthy turkey or flock of healthy turkey are most susceptible to infection with histomoniasis.

3. The method according to claim 1, wherein the feed is supplemented with paromomycin in a range between 10 to 750 parts per million (ppm).

4. A method for reducing or preventing horizontal spread of histomoniasis in a flock of turkey, the method comprising:
    formulating a feed stuff for turkey comprising feed supplemented with paromomycin in an amount sufficient to provide prophylaxis of histomoniasis; and
    feeding the feed stuff to the flock of turkey continuously from day 0 until slaughter or at least for more than one week; whereby horizontal spread of histomoniasis is reduced or prevented in the flock of turkey.

5. The method according to claim 4, wherein the feed is supplemented with paromomycin in a range between 10 to 750 parts per million (ppm).

6. A method for increasing weight gain and improving feed efficiency in turkey or in a flock of turkey, the method comprising:
    formulating a feed stuff for turkey comprising feed supplemented with paromomycin in an amount sufficient to provide prophylaxis of histomoniasis; and
    feeding the feed stuff to the turkey or to the flock of turkey continuously from day 0 until slaughter or at least for more than one week; whereby weight gain is increased and feed efficiency is improved in the turkey or the flock of turkey.

7. The method according to claim 6, wherein the feed is supplemented with paromomycin in a range between 10 to 750 parts per million (ppm).

8. A method for preventing infection with or spread of histomoniasis in healthy turkey or in a flock of healthy turkey, the method comprising:
    providing a feed stuff for turkey comprising feed supplemented with paromomycin in an amount sufficient to provide prophylaxis of histomoniasis; and
    feeding the feed stuff to the healthy turkey or flock of healthy turkey continuously from day 0 until slaughter or at least for more than one week; whereby infection or spread of histomoniasis in the healthy turkey or in the flock of healthy turkey is prevented.

9. The method according to claim 8, wherein the feed is supplemented with paromomycin in a range between 10 to 750 parts per million (ppm).

10. The method according to claim 8, wherein the feeding is applied during a time period when the healthy turkey or flock of healthy turkey are most susceptible to infection with histomoniasis.

11. A method for reducing or preventing horizontal spread of histomoniasis in a flock of turkey, the method comprising:

providing a feed stuff for turkey comprising feed supplemented with paromomycin in an amount sufficient to provide prophylaxis of histomoniasis; and feeding the feed stuff to the flock of turkey continuously from day 0 until slaughter or at least for more than one week; whereby horizontal spread of histomoniasis is reduced or prevented in the flock of turkey.

12. The method according to claim 11, wherein the feed is supplemented with paromomycin in a range between 10 to 750 parts per million (ppm).

13. A method for increasing weight gain and improving feed efficiency in turkey or in a flock of turkey, the method comprising:

providing a feed stuff for turkey comprising feed supplemented with paromomycin in an amount sufficient to provide prophylaxis of histomoniasis; and feeding the feed stuff to the turkey or to the flock of turkey continuously from day 0 until slaughter or at least for more than one week; whereby weight gain is increased and feed efficiency is improved in the turkey or the flock of turkey.

14. The method according to claim 13, wherein the feed is supplemented with paromomycin in a range between 10 to 750 parts per million (ppm).

* * * * *